US006365696B1

(12) United States Patent
Westmeyer et al.

(10) Patent No.: US 6,365,696 B1
(45) Date of Patent: Apr. 2, 2002

(54) PROCESS FOR PRODUCING EPOXYORGANOSILICON COMPOUNDS

(75) Inventors: Mark D. Westmeyer, Marietta, OH (US); Kevin L. Bobbitt, Waverly, WV (US); James S. Ritscher, Marietta, OH (US)

(73) Assignee: Crompton Corporation, Middlebury, CT (US)

(*) Notice: Subject to any disclaimer, the term of this patent is extended or adjusted under 35 U.S.C. 154(b) by 0 days.

(21) Appl. No.: 09/573,111

(22) Filed: May 17, 2000

Related U.S. Application Data

(63) Continuation-in-part of application No. 09/465,603, filed on Dec. 17, 1999, now abandoned.

(51) Int. Cl.$^7$ ............................................. C08G 77/08
(52) U.S. Cl. ..................... 528/12; 524/588; 524/858; 524/861; 528/31; 528/27
(58) Field of Search ................. 524/588, 858, 524/861; 528/31, 27, 12

(56) References Cited

U.S. PATENT DOCUMENTS

| | | |
|---|---|---|
| 4,083,856 A | 4/1978 | Mendicino |
| 4,804,768 A | 2/1989 | Quirk et al. |
| 4,847,398 A | 7/1989 | Mehta et al. |
| 4,966,981 A | 10/1990 | Takai et al. |
| 5,128,431 A | 7/1992 | Riding et al. |
| 5,169,962 A | 12/1992 | Crivello et al. |
| 5,258,480 A | 11/1993 | Eckberg et al. |
| 5,260,399 A | 11/1993 | Crivello et al. |
| 5,270,424 A | 12/1993 | Drake et al. |
| 5,359,111 A | 10/1994 | Kleyer et al. |
| 5,359,112 A | 10/1994 | Drake |
| 5,387,698 A | 2/1995 | Crivello et al. |
| 5,391,676 A | 2/1995 | Eckberg et al. |
| 5,442,026 A | 8/1995 | Crivello et al. |
| 5,583,194 A | 12/1996 | Crivello et al. |
| 5,986,022 A | * 11/1999 | Austin et al. |
| 6,048,994 A | 4/2000 | Tachikawa et al. |
| 6,166,238 A | * 12/2000 | Filipkowski et al. |

FOREIGN PATENT DOCUMENTS

| | | |
|---|---|---|
| JP | 56090092 | 7/1981 |
| JP | 05163286 | 6/1993 |
| JP | 11180986 | 7/1999 |
| SU | 415268 | 11/1974 |

OTHER PUBLICATIONS

Lukevics, E., Latest Research on the Hydrosilylation Reaction, Russian Chemical Reviews, 46(3) (1977) pp. 264–277.
Speier, J, L., Homogeneous Catalysis of Hydrosilation by Transition Metals, Advances in Organometallic Chemistry, vol. 17 (1979) pp. 407–447.
Lewis, L. N., Lewis N., Platinum–Catalyzed Hydrosilylation–Colloid Formation as the Essential Step, J. Am. Chem. Soc. 108, (1986) pp. 7228–7231.
McMullen, A. K. et al., XXVII Organosilicon Symposium, Rensselaer Polytechnic Institute, Troy, New York, Mar. 18–19, 1994.
Schilling, Jr., Curtis et al., 32$^{nd}$ Organosilicon Symposium, Marquette University, Milwaukee, Wisconsin, Mar. 12–13, 1999.
Stein, J., Lewis, L. N., Gao, Y., Scott, R. A., In Situ Determinatin of the Active Catalyst in Hydrosilylation Reactions Using Highly Reactive Pt(0) Catalyst Precursors, J. Am Chem. Soc., 121 (1999) pp. 3693–3703.
Chalk, A. J., Harrod, J. F., Homogeneous Catalysis. II. The Mechanism of the Hydrosilation of Olefins Catalyzed by Group VIII Metal Complexes, Journal of the American Chemical Society, vol. 87, No. 1, (1965) pp. 16–21.
Harrod, J. F., Chalk, A. J., "Hydrosilation Catalyzed by Group VIII Complexes", Wender, I., *Organic Syntheses via Metal Carbonyls,* vol. 2, (New York, Wiley, 1977) pp. 673–704.
Crivello, J. V., Fan, M., Novel Platinum–Containing Initiators for Ring–Opening Polymerizations, Journal of Polymer Science: Part A: Polymer Chemistry, vol. 29 (1991) pp. 1853–1863.
Crivello, J. V., Fan, M., Novel Platinum Intitators for Ring–Opening Polymerizations, Polymer Preprints, vol. 32, (1991) pp. 338–341.
Crivello, J. V., Lee, J. L., The Synthesis, Characterization, and Photoinitiated Cationic Polymerization of Silicon–Containing Epoxy Resins, Journal of Polymer Science: Part A: Polymer Chemistry, vol. 28, (1990) pp. 479–503.
Crivello, J. V., Fan, M., Regioselective Ring–Opening Polymerizations and Hydrosilations Catalyzed by Transition Metals, Macromol. Chem., Macromol. Symp. 54/55 (1992) pp. 189–198.
Chalk, A. J., Group IV—Cobalt Complexes as Catalysts for Silylation and Cyclic Ether Polymrization, Chemical Communications (1970) pp. 847–848.
Schweizer, A. E., Kerr, G. T., Thermal Decomposition of Hexachloroplatinic Acid, Inorganic Chemistry, vol. 17, No. 8 (1978) pp. 2326–2327.
Lewis, L. N. Chemistry Catalysis by Colloids and Clusters, Chem. Review 93 (1993) pp. 2693–2730.

* cited by examiner

*Primary Examiner*—Robert Dawson
*Assistant Examiner*—Kuo-Liang Peng
(74) *Attorney, Agent, or Firm*—Michael P. Dilworth

(57) ABSTRACT

The present invention describes a method for producing epoxyorganosilicon compounds through the platinum-catalyzed hydrosilation reaction of ethylenically unsaturated epoxides and a silicon-hydride in the presence of a carboxylic acid salt. Also taught herein is the use of carboxylic acid salts in compositions of epoxyorganosilicon compounds to provide compositions of greater stability.

6 Claims, No Drawings

US 6,365,696 B1

PROCESS FOR PRODUCING EPOXYORGANOSILICON COMPOUNDS

CROSS REFERENCE TO RELATED APPLICATIONS

This application is a continuation-in-part of application Ser. No. 09/465,603, filed Dec. 17, 1999, now abandoned.

BACKGROUND OF THE INVENTION

In the production of silicon compositions, transition metal catalysts have long been known to promote the hydrosilation reaction. In addition to catalyzing the hydrosilation reaction, many transition metals, in the presence of silicon hydrides (Si—H), also promote epoxide ring-opening polymerization of the ethylenically unsaturated epoxide starting material and the epoxysilane or epoxysilicone product of the hydrosilation reaction. This epoxide ring-opening polymerization reaction during production of an epoxysilane or epoxysilicone can lead to gelation, and may result in both the loss of the entire batch and in considerable loss of time to remove the insoluble gelled resin. Additionally, a partial gelation can occur during epoxysilicone synthesis such that reproducible batch-to-batch viscosities of the epoxysilicone product may be difficult to obtain.

In the presence of precious metal hydrosilation catalysts, e.g., chloroplatinic acid, epoxysilicones have been found to gel slowly on storage at room temperature due to the epoxide ring-opening polymerization, thus shortening the shelf life of the epoxysilicone product. This storage problem can be partially alleviated by adding a hydrochloride acceptor to the reaction to sequester HCl present from decomposition of the catalyst, as reported in U.S. Pat. No. 4,083,856 (F. Mendicino).

The prior art has taught that the epoxide ring-opening polymerization side reaction does not occur in the rhodium-catalyzed hydrosilation reaction of an ethylenically unsaturated epoxide and a Si—H. For example, U.S. Pat. No. 5,442,026 (Crivello et al.), U.S. Pat. No. 5,169,962 (Crivello et al.), U.S. Pat. No. 4,804,768 (Quirk et al.) teach that rhodium catalysts such as Wilkinson's catalyst, $RhCl_3$ hydrate, $RhH(CO)(PPh_3)_3$ can be used to produce epoxysilicones. In addition to rhodium catalysts, certain platinum catalyst systems have been reported to selectively catalyze the hydrosilation reaction of ethylenically unsaturated epoxides and a Si—H versus the epoxide ring-opening polymerization side reaction, as disclosed in U.S. Pat. No. 5,583,194 (Crivello et al.) which teaches that quaternary onium hexachloroplatinate salts, e.g., $(R_4M)_2PtCl_6$, or as disclosed U.S. Pat. No. 5,260,399 (Crivello et al.) transition metal phosphine complexes, e.g., $Pt(PPh_3)_4$, can be used to produce epoxysilicon compositions. However, these catalysts have not achieved commercial acceptance yet.

U.S. Pat. Nos. 5,240,971, 5,227,420, and 5,258,480 (Eckberg et al.) reported the preparation of epoxysilicones using either $RhCl_3[S(n-Bu)_2]_3$ or $PtCl_2(SEt_2)_2$ as the catalyst in the presence of a tertiary amine to control the viscosity during the hydrosilation reaction. However, only a limited number of transition metal catalysts are active in the presence of this stabilizer.

Carboxylic acids have been reported to promote the transition metal catalyzed hydrosilation reaction, as disclosed in JP 11 180,986 (M. Tachhikawa; K. Takei), F. Mendicino; C. Schilling Jr. *Abstract of Papers*, $32^{nd}$ Organosilicon Symposium; 1999; P-68, and in UDC 415,268 (Belyakova et al.). But, carboxylic acid salts have not. Carboxylic acid salts have been reported to prevent acetal formation through the hydroxyl groups of a silicone polyether copolymer as disclosed in U.S. Pat. No. 4,847,398 (K. R. Mehta et al.); however, no utility for epoxides is disclosed.

The literature does mention that alcohols prevent or retard the epoxide ring-opening polymerization reaction (A. K. McMullen; et al. *Abstract of Papers*, $27^{th}$ Organosilicon Symposium, 1994; Abstract P-45; and Crivello et al. Polym. Preps. 1991, 32, 338).

It is apparent that there exists a need in the industry for a method to eliminate epoxide ring-opening polymerization, and olefin isomerization when commonly used hydrosilation catalysts, such chloroplatinic acid, are employed. There is also a need for an efficient yet economical method of producing epoxysilicone monomers and oligomers in the absence of the epoxide ring-opening polymerization reaction, thereby generating epoxysilicon compositions of reproducible batch-to-batch viscosity. There is additionally a need for epoxysilicon compositions that are stable to the epoxide ring-opening polymerization reaction and therefore have increased the shelf life without an additional processing step.

SUMMARY OF INVENTION

The object of this invention is to provide a method for preparing epoxy organosilicon compositions through the platinum metal-catalyzed hydrosilation reaction between an ethylenically unsaturated epoxide and a hydrido organosilicon in the presence of a carboxylic acid salt where the catalyst efficiently promotes the hydrosilation reaction without also promoting either the epoxide ring-opening polymerization reaction of either the ethylenically unsaturated epoxide starting material, the epoxysilicon composition or the isomerization of the ethylenically unsaturated epoxide starting material. Compositions of epoxy organosilicon compounds and the salt of the carboxylic acid are taught as well wherein the salt suppresses the reactivity of the epoxy functionality.

DETAILED DESCRIPTION OF THE INVENTION

According to the process of the invention, the platinum-catalyzed hydrosilation of an ethylenically unsaturated epoxide with either a hydrido silane or hydrido siloxane occurs in the presence of a carboxylic acid salt without epoxide ring-opening polymerization side reaction, allowing for the production of high yields of epoxyorgano silanes or siloxanes. For certain carboxylic acid salts, both epoxide ring-opening polymerization and olefin isomerization are suppressed. This inventive process allows for greater batch-to-batch consistencies without the use of more complex catalyst systems. While the process is useful for both siloxanes and silanes, given that the internal rearrangement of the olefin is more of an issue in the hydrosilation of a silane, the present invention will find greater utility in the hydrosilation of hydrido alkoxysilanes.

These salts are also useful for the suppression of the reactivity of the epoxide after the hydrosilation reaction and thus are useful to extend the shelf life of epoxy organosilicon materials, even if post added after hydrosilation.

Ethylenically unsaturated epoxides for use herein include linear or cycloaliphatic epoxy compounds wherein the unsaturation is terminal (i.e., ±, $^2$) which contain from 4 to 50 carbon atoms. The epoxide may be visualized as an ethylenically unsaturated epoxide of the formula:

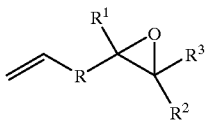

where R can be a single bond or an alkylene optionally containing alkyl pendant groups; $R^1$, $R^2$ and $R^3$ can individually be hydrogen, alkyl straight, branched or cyclic, or any two of $R^1$, $R^2$ or $R^3$ can be alkylene and combined to form a 5 to 12 carbon cyclic ring, optionally containing alkyl pendants; and the number of carbon atoms in R, $R^1$, $R^2$, and $R^3$ are such that the total number of carbon atoms in the epoxide is from 4 to 50. Some representative epoxides are: 4vinylcyclohexene monoxide, 1-methyl-4-isopropenyl cyclohexene monoxide, and butadiene monoxide. The preferred epoxide is 4-vinylcyclohexene monoxide.

The hydridosilanes may be alkoxy silanes. The hydrido alkoxysilanes that may be used include the trialkoxysilanes, such as trimethoxysilane, triethoxysilane, tri-n-propoxysilane, and triisopropoxysilane. Trimethoxysilane and triethoxysilane are preferred. Other hydroalkoxysilanes include dialkoxysilanes such as methyldimethoxysilane, methyldiethoxysilane, dimethylmethoxysilane, and dimethylethoxysilane. Hydrosilanes in general can be represented by the formula $R^4{}_n(OR^4)_{3-n}SiH$, wherein $R^4$ is a branched or linear alkyl group of 1 to 18 carbon atoms, a cyclic alkyl group of four to eight carbon atoms or an aryl, alkaryl, an aralkyl group of six to twelve carbon atoms, optionally containing halogen, oxygen, or nitrogen substituents with the proviso that such substituents do not interfere with either hydrosilation or promotion, and n is an integer selected from 0, 1, and 2. $R^4$ is preferably a $C_1$–$C_2$ alkyl wherein n is preferably 1 or 0.

The hydrido organosiloxanes have the general formula:

wherein $R^5$ represents a monovalent hydrocarbon radical, a has a value of from 1 to 2.99, b has a value of from 0.001 to 1, and the sum of a+b has a value of from 1.5 to 3.0 and n=2 to 400. More specifically, examples of the silicone hydride are heptamethyltrisiloxane (MD'M), tetramethyldisiloxane (M'M'), cyclic siloxanes $D_jD'_k$, and linear siloxanes $MD_xD'_yM$, wherein M=—$O_{1/2}Si(CH_3)_3$, M'=—$O_{1/2}Si(H)(CH_3)_2$, D'=—OSi(H)(CH_3)—, D=—OSi(CH_3)_2—, j=1 to 8, k≧1 and j+k=4 to 8, x=0 to 200 and y=1 to 200. Preferably j+k=4 to 5, x=1 to 20 and y=1 to 50.

The salt of the carboxylic acid may be represented by the formula $R^6CO_2M$ wherein M represents an alkali, alkaline earth, transition metal, or an ammonium ion and $R^6$ represents a monovalent hydrocarbon of one to 18 carbon atoms, which may be substituted with amino groups, hydroxyl functionalities, carboxyl groups or ester groups. Preferably $R^6$ is a linear or branched alkyl of one to ten carbons or an aryl or alkaryl of 6 to 12 carbons. Specific examples of carboxylic acid salts include one or more salts of the alkali metals, e.g., lithium acetate, sodium acetate, potassium acetate, potassium benzoate, sodium trifluoroacetate or sodium propionate, of the alkaline earth metals, e.g., calcium acetate, of the transition metals, e.g., samarium (III) acetate, copper (II) acetate, copper (II) ethylhexanoate, indium (III) acetate, and nonquaternary ammonium or phosphonium, e.g., ammonium formate, ammonium acetate, ammonium isovalerate, ammonium 2ethylbutyrate, ammonium propionate or combinations of salts such as ammonium chloride and sodium acetate are suitable with this process, with ammonium salts of carboxylic acids being preferred, and ammonium propionate being the most preferred carboxylate salt. The acid may be a hydroxy acid, but only when the organosilicon hydride is an organosiloxane. The acid may be an amino acid, e.g., lysine or glutamic acid, but said acids are not preferred since they do not reduce olefin isomerization. Polymeric acids, such as polyacrylic acid may be used, in which case some of the acid may be left in acid form, i.e., it does not have to be neutralized to the salt form.

In the method of this invention, the present carboxylic acid salts are most useful in the range of 1 to about 10000 parts per million (ppm), preferably in the range of 200 to about 5000 ppm, and most preferably in the range of 100 to about 500 ppm based upon the weight of the ethylenically unsaturated epoxide.

The platinum catalyst can be of any form of platinum, which catalyzes the hydrosilation reaction of an ethylenically unsaturated epoxide and a silicon hydride. Platinum catalysts useful in the process of the invention include: hexachloroplatinic acid, various solutions derived from chloroplatinic acid, tris(tetramethyldivinyldisiloxane) diplatinum (0), phosphine complexes of platinum, and bis (acetylacetonate)platinum (II). The preferred catalyst in the practice of this invention is derived from a solution of hexachloroplatinic acid, where the most preferable catalyst is derived from a 10% (wt/wt) solution of hexachloroplatinic acid in ethanol. In the method of this invention, said catalysts are most useful in the range of 1 to about 5000 parts per million (ppm), preferably in the range of 1–500 ppm, and most preferred in the range of 5–50 ppm of platinum, based upon the weight of the combined weight of both the ethylenically unsaturated epoxide and SiH containing reactant.

This reaction can be carried out over a wide range of temperatures and pressures; however, the usual temperature range is from 50° C. to about 175° C. with the preferred temperature range being from about 75° C. to 125° C. The preferred pressure is atmospheric pressure. The duration of the reaction will be dependent on catalyst concentration and the reaction temperature. At higher catalyst concentrations and temperatures, the reaction will require less reaction time. The residence time within the reactor is not critical but should be sufficient to achieve a satisfactory degree of conversion to the hydrosilated product, i.e., >80%, within acceptable limits given the volume of the equipment and the desired rate of production. Typical acceptable residence times are on the order of 0.5 to 4 hours. The reaction is usually conducted with no solvent, although a solvent may be used. Any hydrocarbon may be used such as octane, toluene or xylene.

This reaction can be conducted in the presence of excess olefin or silicon hydride, where the preferred reaction conditions are with a molar excess of olefin. The usual substrate concentration for conducting the reaction is either a 1.5:1.0 to a 1.0:1.5 molar ratio of olefin to silicon hydride (based on moles of hydrogen), preferably a ratio of 1.0:1.0 to 1.5:1.0 and preferred conditions are a 1.01:1.0 to 1.20:1.0 molar ratio of olefin to silicon hydride. The preferred catalyst system can be generated by mixing the catalyst and carboxylic acid salt in the olefin or the carboxylic acid salt can be added to the silicon composition after the hydrosilation reaction is complete. A catalyst promoter such as a carboxylic acid or an alcohol may be used with the carboyxlic acid salt, if necessary.

The resulting product may be purified for use, e.g., by stripping or distillation, as required.

The hydrosilation may be conducted batchwise, semi-batchwise or continuously as is known in the art.

EXAMPLES

The following illustrative and comparative examples are intended to describe the present invention in more detail; however, they are not meant to limit the scope of the specification and claims. All parts and percentages presented in the examples below are by weight unless otherwise specified. The abbreviations g, mL, VCMX, CPA, Si—H, AcOH, MeOH, EtOH, IPA, cSt and GC stand for, respectively, gram, milliliter, 4-vinylcyclohexene monoxide, solution consisting of 10% (wt/wt) of hexachloroplatinic acid in ethanol, any silicon hydride-containing species, acetic acid, methanol, ethanol, isopropanol, centistokes and gas chromatography. An internal standard was used in order to determine the percent of uneluted heavies for each GC analysis. Uneluted heavies are defined as all components that did not elute under the GC conditions employed for the specific analysis. An *indicates no internal standard was used.

COMPARATIVE EXAMPLES

For Example 1—at room temperature, 21.98 g of neat VCMX was treated with 0.018 ml of CPA and warmed. At 90° C., the VCMX solution was reacted with 20.46 g of $(MeO)_3SiH$. After the $(MeO)_3SiH$ addition was completed, the solution was maintained at 90° C. After ~30 minutes, a vigorous exothermic reaction occurred accompanied with an increase in viscosity of the solution and eventual solidification (or gelation).

For Examples 2–15—all reactions were conducted using a 10% molar excess of VCMX (97% purity) versus $(MeO)_3SiH$ and the specified catalyst system at 90° C. followed by one hour at 90° C. after the addition was completed. All solutions were analyzed using gas chromatography.

Example 2—At room temperature, 19.18 g of neat VCMX was treated with 0.005 g of $Pt(PPh_3)_4$, 0.040 ml of MeOH, and 0.040 ml of AcOH and warmed. At 90° C., the VCMX solution was reacted with 17.10 g of $(MeO)_3SiH$. After the $(MeO)_3SiH$ addition was completed, the solution was maintained at 90° C. for one hour. The results are in the table below with other comparative experiments run under similar conditions.

TABLE 1

Comparative examples for the transition metal-catalyzed hydrosilation reaction of VCMX and $(MeO)_3SiH$.

| Examples | Catalyst System[a] | $(MeO)_3SiH$ | $(MeO)_4Si$ | VCMX | VCMX isomer | product | uneluted heavies |
|---|---|---|---|---|---|---|---|
| 2 | $Pt(PPh_3)_4$ (10 ppm Pt) | 0.2 | 1.4 | <0.1 | 2.5 | 90.5 | 2.2 |
| 3 | $RhCl_3$ hydrate (50 ppm Rh) and 250 ppm tetrabutylammonium bromide | 1.7 | 16.6 | 2.3 | 33.1 | 34.3 | 5.6 |
| 4 | $K_2PtCl_6$ (50 ppmn Pt) and 250 ppm tetrabutylammonium chloride | 1.8 | 17.2 | 55.6 | 16.1 | 4.3 | * |
| 5 | CPA (10 ppm Pt) and 250 ppm tetramethylammonium chloride | 0.5 | 1.1 | 0.3 | 5.9 | 47.2 | 42.9 |
| 6 | CPA (10 ppm Pt) and 250 ppm tetraethylammonium chloride | 2.2 | 30.0 | 28.6 | 14.6 | 8.8 | 9.3 |
| 7 | CPA (10 ppm Pt) and 116 ppm tetrabutylammonium chloride | 6.2 | 25.4 | 23.6 | 16.6 | 18.0 | 5.0 |
| 8 | CPA (10 ppm Pt) and 180 ppm benzyltributylammonium chloride | 16.8 | 3.2 | 62.6 | 10.3 | 1.1 | * |
| 8 | $RhCl_3$ hydrate (258 ppm Rh) and 500 ppm triphenylphosphine | <0.1 | 4.9 | 2.0 | 1.2 | 69.3 | 8.0 |
| 9 | $RhCl_3$ hydrate (107 ppm Rh) | <0.1 | 1.3 | 0.8 | 4.0 | 86.4 | 3.9 |
| 10 | $RhCl_3[S(n-Butyl)_2]_3$ (48 ppm Rh) | <0.1 | 1.0 | 3.4 | 3.8 | 88.0 | 1.0 |
| 11 | $RhCl_3[S(n-Butyl)_2]_3$ (26 ppm Rh) | <0.1 | 1.1 | 5.8 | 1.9 | 86.34 | 1.7 |
| 12 | $RhCl_3[S(n-Butyl)_2]_3$ (8 ppm Rh) | 16.3 | 1.3 | 74.4 | 1.8 | 3.3 | * |
| 13 | Karstedts catalyst (10 ppm Pt) | 0.2 | 1.5 | 0.2 | 4.7 | 57.8 | 31.8 |

[a]All reactions were conducted using a 10% molar excess of VCMX (97% purity) verus $(MeO)_3SiH$ at 90° C. followed by one hour at 90° C. after the addition was completed.

Example 14—At room temperature, 19.23 g of neat VCMX was treated with 0.004 g of $Pt(PPh_3)_4$, 0.090 ml of EtOH, 0.018 ml of AcOH and warmed. At 90° C., the VCMX solution was reacted with 23.14 of $(EtO)_3SiH$. After the $(EtO)_3SiH$ addition was completed, the solution was maintained at 90° C. for one hour.

| $(EtO)_3SiH$ | $(EtO)_4Si$ | VCMX | VCMX Isomer | Product | Uneluted Heavies |
|---|---|---|---|---|---|
| 7.6 | 0.9 | 14.3 | 1.5 | 69.8 | * |

Example 15—At room temperature, 20.11 g of neat VCMX was treated with 0.070 ml of $RhCl_3[S(n-Bu)_2]_3$, 0.023 ml of AcOH, 0.11 ml of EtOH, and warmed. At 90° C., the VCMX solution was reacted with 24.0 g of $(EtO)_3SiH$. After the $(EtO)_3SiH$ addition was completed, the solution was maintained at 90° C. for one hour.

| $(EtO)_3SiH$ | $(EtO)_4Si$ | VCMX | VCMX Isomer | Product | Uneluted Heavies |
|---|---|---|---|---|---|
| 37.2 | 0.4 | 54.6 | 1.3 | 2.9 | * |

EXAMPLES OF THIS INVENTION

General Procedure for the use of Carboxylate Acid Salts in the Pt-catalyzed Hydrosilation Reaction of VCMX and a Silicone Hydride (Si—H):

1.) where Si—H is an organofunctional silane A typical reaction was conducted by treating 1.10–1.30 molar equivalents (vs. Si—H) of VCMX at room temperature with 3000 ppm of an alcohol, 500 ppm of acetic acid (AcOH), a carboxylate acid salt and a catalyst versus total mass of the reaction. Typically, 10 ppm of Pt was sufficient to catalyze the reaction. This solution was warmed. At 90° C., the solution was reacted with 1.00 molar equivalent of Si—H. The solution's temperature was maintained between 90–102° C. throughout the Si—H addition. After the Si—H addition was completed, the solutions temperature was maintained at 90° C. for one hour. After this time, solution was allowed to cool to room temperature.

2.) where Si—H is organfunctional siloxane. A typical reaction was conducted by mixing 1.10–1.30 molar equivalents (vs. Si—H) of VCMX at room temperature with an alcohol, and sodium carbonate. The VCMX solution was treated with an appropriate amount of the Si—H and the solution was warmed. At 90° C., the solution was treated with a catalyst. Typically, 10 ppm of Pt (versus the total mass of the reaction) was sufficient to catalyze the reaction. Once an initial temperature increase was detected, the remaining Si—H fluid was added to the VCMX solution. The solution's temperature was maintained between 90–100° C. throughout the Si—H addition. After the Si—H addition was completed, the carboxylic acid salt was added to the solution if it had not been added prior the hydrosilation reaction. The solution was maintained at 90° C. for one hour. After this time, solution was analyzed for Si—H content. The reaction was deemed to be complete by the absence of Si—H. The reaction mixture was warmed under reduced pressure and stripped of volatile components (primarily unreacted VCMX and the olefin isomer of VCMX) at 150° C. (75–100 mm Hg) for 2–3 hours in order to removed unreacted VCMX. The final product was then filtered through a 5¼ m laboratory filter pad.

For examples 16–38, all reactions were conducted using a 10% molar excess of VCMX (97% purity) versus (MeO)$_3$SiH, 3000 ppm methanol, 500 ppm acetic acid, carboxylic acid salt and 10 ppm Pt as a solution of chloroplatinic acid at 90° C. followed by one hour at 90° C. after the addition was completed. All solutions were analyzed using gas chromatography.

TABLE 2

Examples of the transition metal-catalyzed hydrosilation reaction of VCMX and (MeO)$_3$SiH.

| Examples | Catalyst System[a] | (MeO)$_3$SiH | (MeO)$_4$Si | VCMX | VCMX isomer | product | uneluted heavies |
|---|---|---|---|---|---|---|---|
| 16 | 207 ppm ammonium acetate | 0.3 | 0.8 | 2.9 | 0.4 | 92.8 | 0.3 |
| 17 | 250 ppm ammonium acetate | 1.2 | 2.8 | 4.9 | 0.4 | 87.6 | 0.4 |
| 18 | 125 ppm ammonium acetate | <0.1 | 0.8 | 1.3 | 0.6 | 95.0 | <0.1 |
| 19 | 100 ppm ammonium acetate | <0.1 | 1.0 | 6.6 | 0.4 | 89.2 | <0.1 |
| 20 | 50 ppm ammonium acetate | <0.1 | 1.7 | 3.9 | 0.9 | 89.3 | 1.2 |
| 22 | 25 ppm ammonium acetate | <0.1 | 0.7 | 9.6 | 0.5 | 85.8 | 0.6 |
| 23 | 250 ppm ammonium chloride and 250 ppm sodium acetate | 0.1 | 0.7 | 11.0 | 0.4 | 84.9 | 0.4 |
| 24 | 181 ppm ammonium chloride | 0.2 | 1.0 | 1.0 | 4.9 | 87.1 | 2.9 |
| 25 | 250 ppm ammonium formate | 0.9 | 2.9 | 8.8 | 0.3 | 81.5 | 1.4 |
| 26 | 250 ppm ammonium propionate | <0.1 | 0.6 | 0.5 | 0.7 | 96.2 | <0.1 |
| 27 | 250 ppm ammonium isovalerate | 0.1 | 1.1 | 0.5 | 1.2 | 95.0 | <0.1 |
| 28 | 250 ppm ammonium ethylbutyrate | 0.4 | 1.3 | 0.3 | 0.6 | 74.5 | 21.5 |
| 29 | 250 ppm tetramethylammonium acetate | 21.7 | 4.5 | 12.6 | 12.6 | 41.3 | 1.6 |
| 30 | 250 ppm tetrabutylammonium acetate | 13.2 | 8.8 | 29.5 | 6.5 | 28.2 | 7.9 |
| 31 | 130 ppm sodium acetate | <0.1 | 1.4 | 3.4 | 2.5 | 89 | 1.7 |
| 32 | 250 ppm sodium trifluoroacetate | 9.4 | 0.8 | 9.7 | 3.4 | 74.5 | <0.1 |
| 33 | 104 ppm sodium propionate | <0.1 | 1.0 | 1.6 | 3.7 | 90.2 | 0.3 |
| 34 | 99 ppm sodium propionate | <0.1 | 2.1 | 1.1 | 8.0 | 83.9 | 1.7 |
| 35 | 250 ppm potassium acetate | 18.2 | 1.4 | 23.0 | 0.8 | 54.1 | <0.1 |
| 36 | 250 ppm potassium benzoate | 0.9 | 3.0 | 2.8 | 5.0 | 81.6 | 2.5 |
| 37 | 500 ppm calcium acetate | <0.1 | 0.4 | 4.2 | 2.8 | 80.7 | 10.0 |
| 38 | 250 ppm copper 2-ethylhexanoate | 0.1 | 0.4 | 1.8 | 2.4 | 92.4 | 0.7 |

[a]All reactions were conducted using a 10% molar excess of VCMX (97% purity) versus (MeO)$_3$SiH at 90° C. followed by one hour at 90° C. after the addition was completed.

For examples 39–41, all reactions were conducted using a 10% molar excess of VCMX (97% purity) versus (MeO)$_3$SiH, 3000 ppm methanol, 500 ppm acetic acid, specified carboxylic acid salt and the specified precatalyst at 90° C. followed by one hour at 90° C. after the addition was completed. All solutions were analyzed using gas chromatography.

TABLE 3

Examples for the hydrosilation reaction of VCMX and TMS in the presence of carboxylate salts with alternative Pt catalysts.[a]

| Examples | Catalyst System | (MeO)$_3$SiH | (MeO)$_4$Si | VCMX | VCMX isomer | product | uneluted heavies |
|---|---|---|---|---|---|---|---|
| 39 | (NH$_4$)$_2$PtCl$_6$ (24 ppm Pt) | 47.5 | 0.7 | 48.9 | 1.2 | <0.1 | <0.1 |
| 40 | Pt(PPh$_3$)$_4$ (10 ppm Pt) and 100 ppm sodium propionate | <0.1 | 1.4 | 14.6 | 1.4 | 76.2 | 3.2 |
| 41 | Karstedts catalyst (10 ppm Pt) and 100 | 1.4 | 1.6 | <0.1 | 3.9 | 87.7 | 3.2 |

TABLE 3-continued

Examples for the hydrosilation reaction of VCMX and TMS in the presence of carboxylate salts with alternative Pt catalysts.[a]

| Examples | Catalyst System | (MeO)₃SiH | (MeO)₄Si | VCMX | VCMX isomer | product | uneluted heavies |
|---|---|---|---|---|---|---|---|
| | ppm sodium propionate | | | | | | |

[a]All reactions were conducted in a normal addition using a 10% molar excess of VCMX (97%) and 10 ppm Pt (CPA) at 90° C. followed by a one hour at 90° C. after SiH addition was completed.

For examples 44–55, all reactions were conducted using a 20% molar excess of VCMX (97% purity) versus the specified Si—H, 3000 ppm of an alcohol, 500 ppm acetic acid, specified carboxylic acid salt and 10 ppm Pt as a solution of chloroplatinic acid at 90° C. followed by one hour at 90° C. after the addition was completed. All solutions were analyzed using gas chromatography.

$MD_{26.9}D'_{9.4}M$. After the $MD_{26.9}D'_{9.4}M$ addition was completed, the solution was maintained at 85° C. for one hour. The recation mixture was warmed under reduced pressure and stripped at 150° C. (20 mm Hg) for one to two hours in order to removed unreacted VCMX.

Example 60—At room temperature, 196.80 g of VCMX was treated with 1.47 g of $Na_2CO_3$, 3.27 g of

TABLE 4

Examples of the Pt-catalyzed hydrosilation reaction of VCMX with different SiH.

| Examples | Carboyxlic acid salt[a] | R'R₂SiH | R'R₃Si | VCMX | VCMX isomer | product | uneluted heavies |
|---|---|---|---|---|---|---|---|
| | Trimethoxysilane | R' = R= OMe | | | | | |
| 42 | 250 ppm ammonium acetate | 0.2 | 2.1 | 8.2 | 0.3 | 85.4 | 1.0 |
| 43 | 307 ppm sodium propionate | <0.1 | 3.2 | 2.3 | 7.0 | 82.34 | 1.6 |
| | Triethoxysilane | R' = R = OEt | | | | | |
| 44 | 250 ppm ammonium acetate | 2.8 | 1.6 | 5.3 | 0.4 | 82.4 | 2.9 |
| 45 | 307 ppm sodium propionate | 2.8 | 2.6 | <0.1 | 8.7 | 76.0 | 4.8 |
| | Methylidemethoxysilane | R' = CH₃, R = OEt | | | | | |
| 46 | 250 ppm ammonium acetate | <0.1 | 0.7 | 12.8 | 0.6 | 79.2 | * |
| 47 | 307 ppm sodium propionate | 0.1 | 0.7 | 9.0 | 3.2 | 81.9 | * |
| | Methyldiethoxysilane | R' = CH₃, R = OEt | | | | | |
| 48 | 250 ppm ammoniumn acetate | 0.3 | 1.3 | 8.7 | 0.6 | 84.5 | * |
| 49 | 320 ppm sodium propionate | 0.3 | 0.6 | 5.0 | 3.7 | 83.7 | * |
| | MD'M | | | | | | |
| 50 | 250 ppm ammonium acetate | 44.0 | | 48.7 | 0.1 | 5.7 | * |
| 51 | 307 ppm sodium propionate | 35.0 | | 39.8 | 0.2 | 23.4 | * |
| 52 | 250 ppm ammonium propionate | 45.2 | | 51.1 | 0.1 | 1.1 | * |
| | M'M' | | | | | | |
| 53 | 250 ppm ammonium acetate, no acetic acid | 0.1 | | 10.6 | 1.6 | 82.3 | * |
| 54 | 307 ppm sodium propionate | 0.1 | | 16.1 | 1.6 | 76.9 | * |
| 55 | 250 ppm ammonium propionate | 0.1 | | 21.3 | 1.4 | 71.9 | * |

[a]All reactions were conducted in a normal addition using a 20% molar excess of VCMX (97%) and 10 ppm Pt (CPA) at 90° C. followed by a one hour at 90° C. after SiH addition was completed.

For examples 56 to 57, all reactions were conducted using a 20% molar excess of VCMX (97% purity) versus Si—H, specified carboxylic acid salt and 10 ppm Pt as a solution of chloroplatinic. At room temperature, neat VCMX was treated with a carboxylic acid salt, and CPA and was warmed. At 90° C., the VCMX solution was reacted with $MD_{26.9}D'_{9.4}M$. After the $MD_{26.9}D'_{9.4}M$ addition was completed, the solution was maintained at 90° C. for one hour. The reaction mixture was warmed under reduced pressure or stripped at 150° C. (20 mm Hg) for one hour in order to removed unreacted VCMX.

For examples 58 to 60, all reactions were conducted using a 20% molar excess of VCMX (97% purity) versus Si—H and 6 ppm Pt as a solution of chloroplatinic acid. At room temperature, neat VCMX was treated with $Na_2CO_3$, propyleneglycol, tetraethyleneglycol, and $MD_{26.9}D'_{9.4}M$ (10% of total Si—H), and was warmed. At 80° C., the VCMX solution was reacted with the remaining propyleneglycol, 0.57 g of tetraethyleneglycol, 37.09 g of $MD_{26.9}D'_4M$ (10% of total Si—H) and warmed. At 80° C., 0.11 mL of CPA was added to the VCMX solution resulting in an exothermic reaction. The remaining 333.81 g of $MD_{26.9}D'_{9.4}M$ was added to the VCMX solution over the course of one hour. The solution's temperature was maintained between 80–90° C. throughout the Si—H addition. After the $MD_{26.9}D'_{9.4}M$ addition was completed, 1.20 g of sodium propionate was added to the crude silicone composition and the solution's temperature was maintained at 85° C. for thirty minutes. An aliquot of the solution was analyzed for Si—H content. After this time solution was stripped at 3.5 mm Hg and 150° C. in order to removed unreacted VCMX. After 1.5 hours, the solution was allowed to cool to room temperature. Recoverded 37.16 g of unreacted VCMX and its olefin isomer. The final product was then filtered through a 5 µm laboratory filter pad.

TABLE 5

Results from the Pt-catalyzed hydrosilation reaction of VCMX and an organohydrogensiloxane.[a]

| Example | Carboxylic acid salt | [Si—H] | Viscosity (cSt) | Epoxy content |
|---|---|---|---|---|
| 56 | 250 ppm ammonium acetate | not detected | 572 | 10.16% |
| 57 | 250 ppm tetrabutylammonium acetate | no reaction | — | — |
| 58 | No sodium propionate used | not detected | 3021 | not measured |
| 59 | No sodium propionate used | not detected | >10000 | not measured |
| 60 | 2094 ppm sodium propionate | not detected | 438 | 9.71% |

[a]All reactions were conducted in a normal addition using a 20% molar exccess of VCMX (97%) followed by one hour at 90° C. after Si—H addition was completed.

We claim:

1. A process comprising reacting a) an ethylenically unsaturated epoxide of the formula:

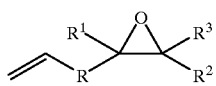

where R is a single bond or an alkylene optionally containing alkyl pendant groups; $R^1$ is a hydrogen, alkyl, straight, branched, or cyclic; $R^2$ and $R^3$ are individually hydrogen, straight, branched or cyclic alkyl, or any two of $R^1$, $R^2$ and $R^3$, taken together are alkylene and, combined with the carbon atom or atoms to which they are attached, form a 5 to 12 carbon cyclic ring, optionally containing alkyl pendants; and the number of carbon atoms in R, $R^1$, $R^2$, and $R^3$ are such that the total number of carbon atoms in the epoxide is from 4 to 50, with (b) an alkoxysilane with the general formula $R^4{}_n(OR^4)_{3-n}SiH$ wherein $R^4$ is a branched or linear alkyl group of 1 to 18 carbon atoms, a cyclic alkyl group of four to eight carbon atoms or an aryl, alkaryl, or aralkyl group of six to twelve carbon atoms, optionally containing halogen, oxygen, or nitrogen substituents with the proviso that such substituents do not interfere with either hydrosilation or promotion, and n is an integer selected from 0, 1, and 2, in the presence of (c) a catalytically effective amount of a platinum catalyst and (d) an ammonium propionate or a sodium propionate.

2. The process of claim 1 wherein the alkoxysilane is trimethoxysilane, triethoxysilane, methyldimethoxysilane or methyldiethoxysilane.

3. The process in claim 1 wherein the ethylenically unsaturated epoxide is 4-vinylcyclohexene monoxide or butadiene monoxide.

4. The process in claim 1 wherein the carboxylic acid salts is represented by the formula: $R^6CO_2M$ wherein M is selected from the group consisting of an alkali, alkaline earth, transition metal, and an ammonium ion and $R^6$ represents a monovalent hydrocarbon of one to 50 carbon atoms, optionally substituted with amino, hydroxyl, carboxyl or ester groups.

5. The process in claim 4 wherein $R^6$ is a linear or branched alkyl of one to ten carbon atoms.

6. The process in claim 1 wherein the platinum catalyst is a solution of chloroplatinic acid.

* * * * *